(12) United States Patent
Brugger et al.

(10) Patent No.: US 7,470,265 B2
(45) Date of Patent: Dec. 30, 2008

(54) DUAL ACCESS SPIKE FOR INFUSATE BAGS

(75) Inventors: James Brugger, Newburyport, MA (US); Kenneth E. Buckler, Methuen, MA (US)

(73) Assignee: NxStage Medical, Inc., Lawrence, MA (US)

( * ) Notice: Subject to any disclaimer, the term of this patent is extended or adjusted under 35 U.S.C. 154(b) by 297 days.

(21) Appl. No.: 10/393,185

(22) Filed: Mar. 20, 2003

(65) Prior Publication Data

US 2005/0277906 A1    Dec. 15, 2005

(51) Int. Cl.
*A61B 19/00* (2006.01)

(52) U.S. Cl. .................. 604/412; 604/411; 604/413; 604/414

(58) Field of Classification Search ......... 604/411–416, 604/905, 86, 87, 148, 200, 201, 204, 533, 604/284, 43, 44, 272–274, 181, 183, 186, 604/104, 239
See application file for complete search history.

(56) References Cited

U.S. PATENT DOCUMENTS

| | | | | |
|---|---|---|---|---|
| 2,409,343 | A * | 10/1946 | Curtis | 604/411 |
| 3,484,849 | A * | 12/1969 | Maenz et al. | 137/575 |
| 3,788,524 | A * | 1/1974 | Davis et al. | 222/209 |
| 4,133,314 | A * | 1/1979 | Bloom et al. | 604/405 |
| 4,439,179 | A | 3/1984 | Lueders et al. | |
| 4,787,898 | A * | 11/1988 | Raines | 604/411 |
| 4,873,991 | A * | 10/1989 | Skinner | 600/567 |
| 4,889,529 | A * | 12/1989 | Haindl | 604/274 |
| 5,024,657 | A | 6/1991 | Needham et al. | |
| 5,445,630 | A * | 8/1995 | Richmond | 604/411 |
| 5,533,647 | A * | 7/1996 | Long-Hsiung | 222/83 |
| 5,698,090 | A | 12/1997 | Bene et al. | |
| 5,702,597 | A | 12/1997 | Chevallet et al. | |
| 5,725,776 | A | 3/1998 | Kenley et al. | |
| 5,744,027 | A | 4/1998 | Connell et al. | |
| 5,762,805 | A | 6/1998 | Truitt et al. | |
| 5,772,624 | A | 6/1998 | Utterberg et al. | |
| 5,776,345 | A | 7/1998 | Truitt et al. | |
| 5,808,181 | A | 9/1998 | Wamsiedler et al. | |
| 5,846,419 | A | 12/1998 | Nederlof | |
| 5,858,006 | A * | 1/1999 | Van der AA et al. | 604/239 |
| 5,863,421 | A | 1/1999 | Peter, Jr. et al. | |
| 5,871,694 | A | 2/1999 | Beden et al. | |
| 5,895,368 | A | 4/1999 | Utterberg | |
| 5,919,154 | A | 7/1999 | Toavs et al. | |
| 5,951,870 | A | 9/1999 | Utterberg | |
| 6,004,302 | A * | 12/1999 | Brierley | 604/264 |
| 6,039,877 | A | 3/2000 | Chevallet et al. | |
| 6,042,784 | A | 3/2000 | Wamsiedler et al. | |
| 6,132,616 | A | 10/2000 | Twardowski et al. | |
| 6,261,267 | B1 * | 7/2001 | Chen | 604/247 |

(Continued)

*Primary Examiner*—Leslie R Deak
(74) *Attorney, Agent, or Firm*—Miles & Stockbridge, PC; Mark A. Catan

(57) ABSTRACT

A port spike for medical fluid containers, such as infusate bags, for example, provides two ports to permit recirculation of fluids within the container. The recirculating flow allows bubbles to settle out which can't happen effectively if the flow is sucked out immediately after entering the container. The spike provides two openings inside the container which prevent such short-circuit flow by ensuring that fluid entering the container is not greatly affected by the suction zone of the flow leaving the container.

19 Claims, 6 Drawing Sheets

U.S. PATENT DOCUMENTS

| | | |
|---|---|---|
| 6,284,131 B1 | 9/2001 | Hogard et al. |
| 6,409,708 B1 * | 6/2002 | Wessman .................... 604/284 |
| 6,474,375 B2 * | 11/2002 | Spero et al. ................. 141/329 |
| 6,517,508 B1 | 2/2003 | Utterberg et al. |
| 6,645,166 B2 | 11/2003 | Scheunert et al. |
| 6,669,709 B1 | 12/2003 | Cohn et al. |
| 6,726,672 B1 * | 4/2004 | Hanly et al. ................ 604/414 |
| 6,979,309 B2 | 12/2005 | Burbank et al. |
| 2004/0054321 A1 | 3/2004 | Schon et al. |
| 2004/0122418 A1 | 6/2004 | Voorhees |
| 2005/0020958 A1 | 1/2005 | Paolini et al. |
| 2005/0045540 A1 | 3/2005 | Connell et al. |
| 2005/0061740 A1 | 3/2005 | Felding et al. |
| 2005/0065459 A1 | 3/2005 | Zhang et al. |
| 2005/0090774 A1 | 4/2005 | Tonelli et al. |
| 2005/0171469 A1 | 8/2005 | Cunningham |
| 2005/0251086 A1 | 11/2005 | Stemby |
| 2005/0288623 A1 | 12/2005 | Hjalmarsson |

* cited by examiner

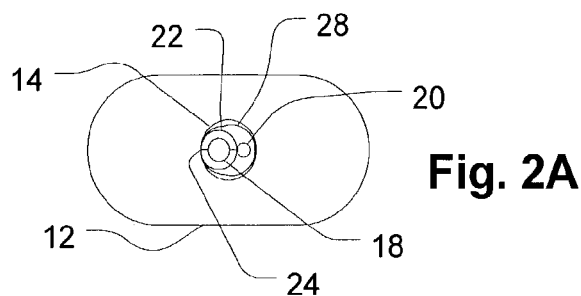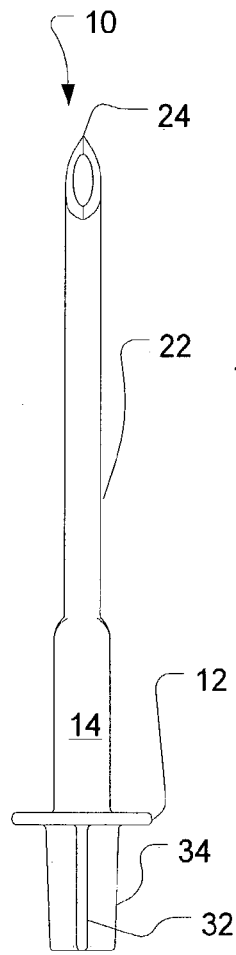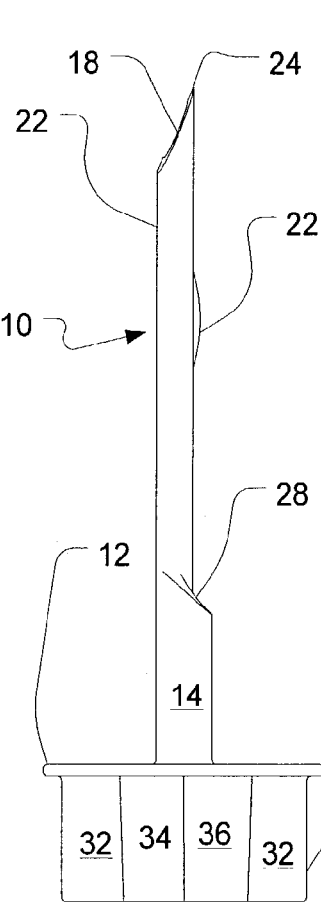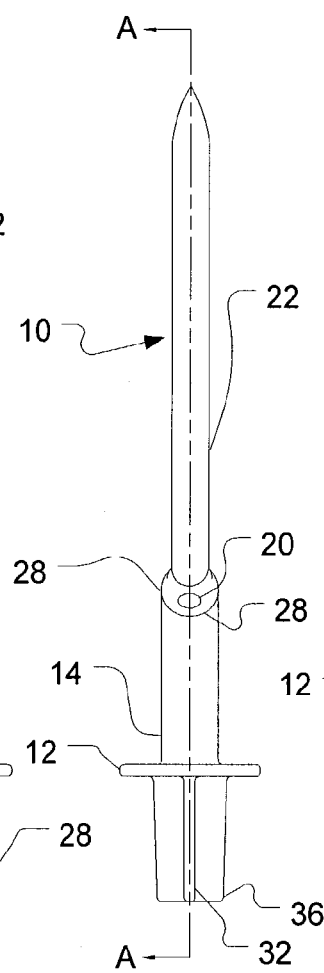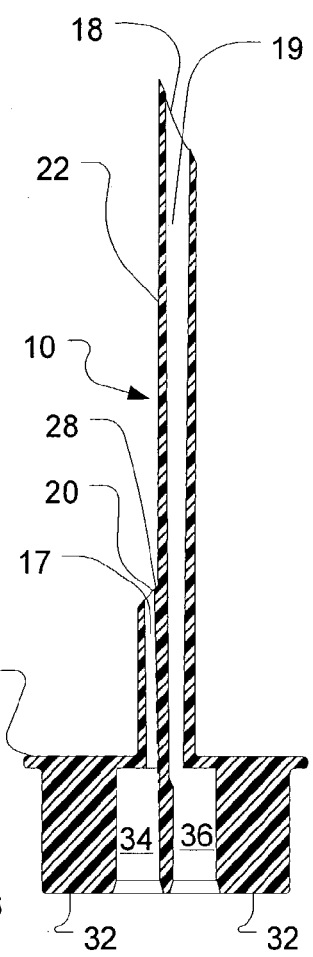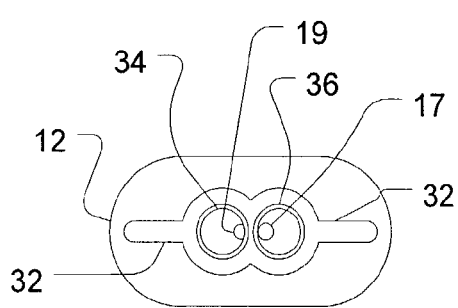

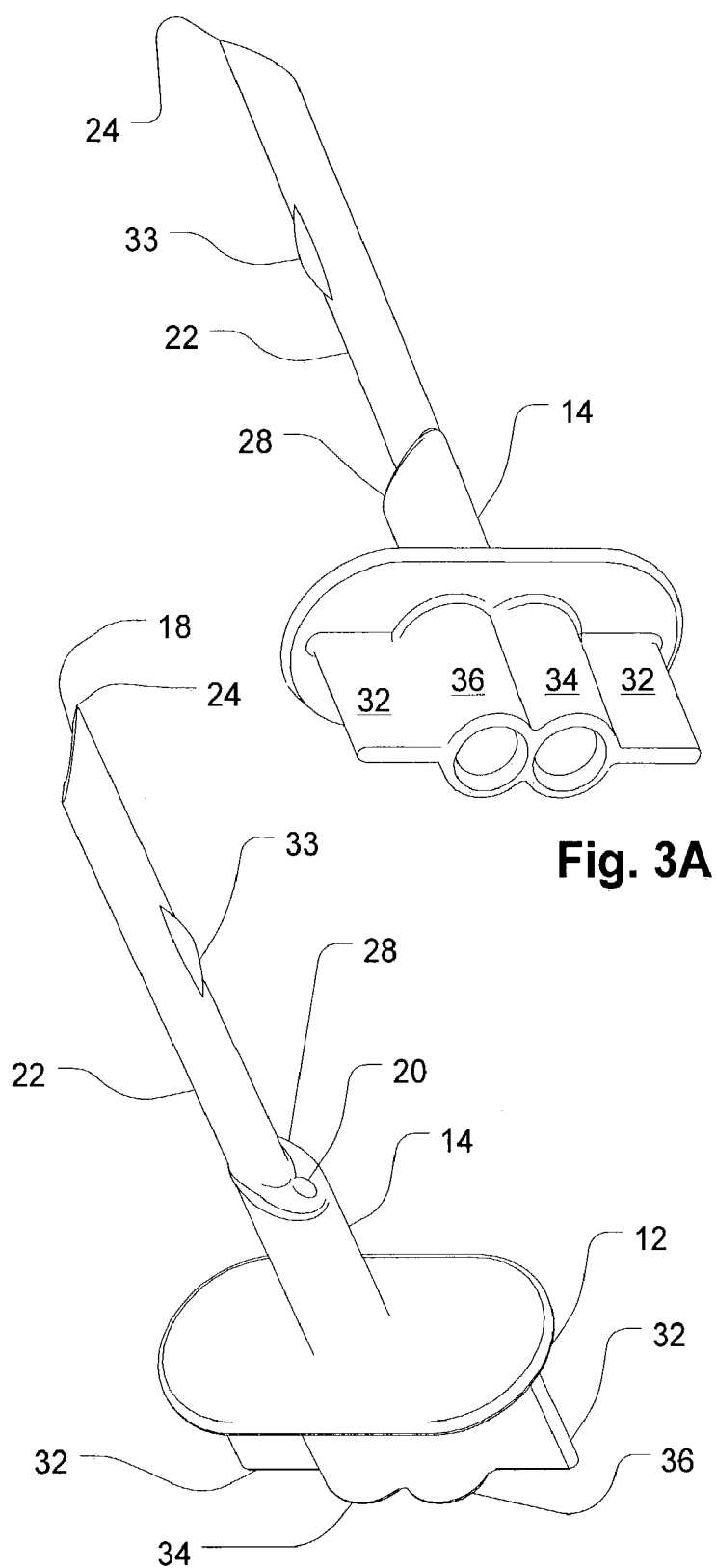
Fig. 3A
Fig. 3B
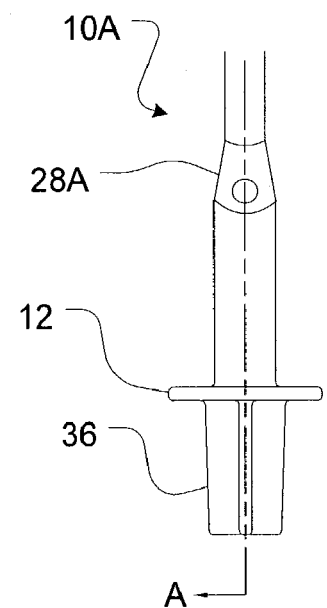
Fig. 3C

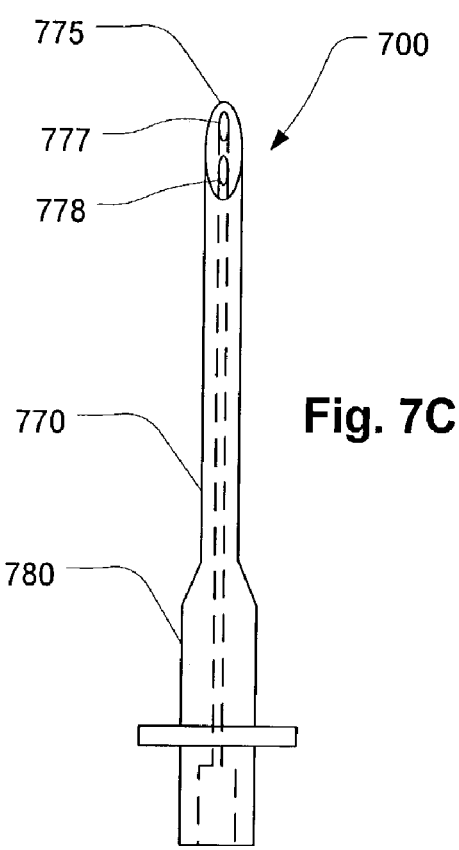
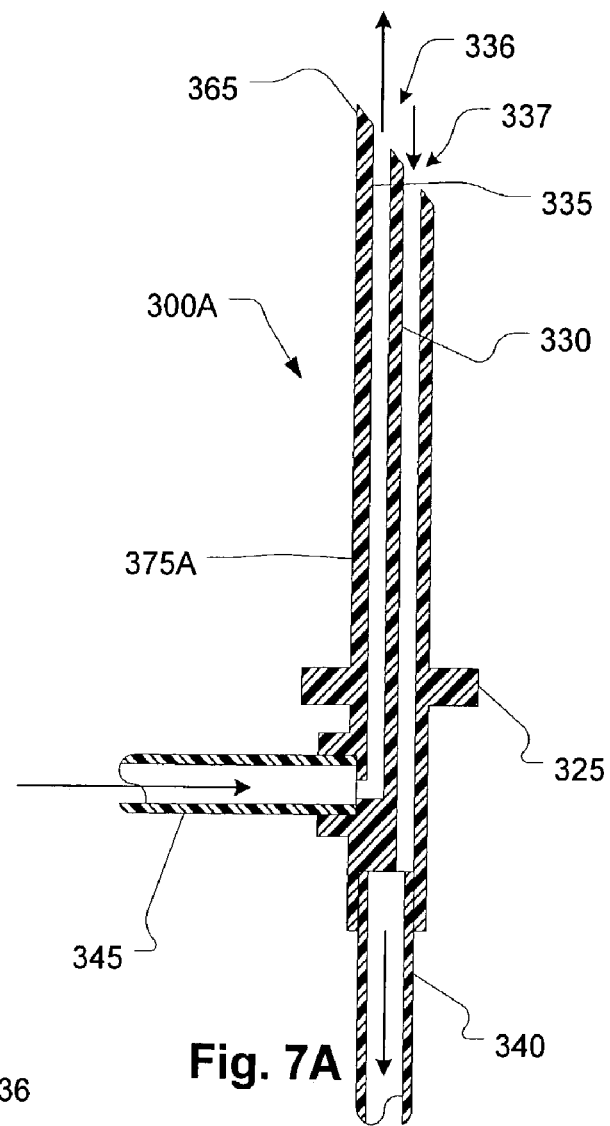
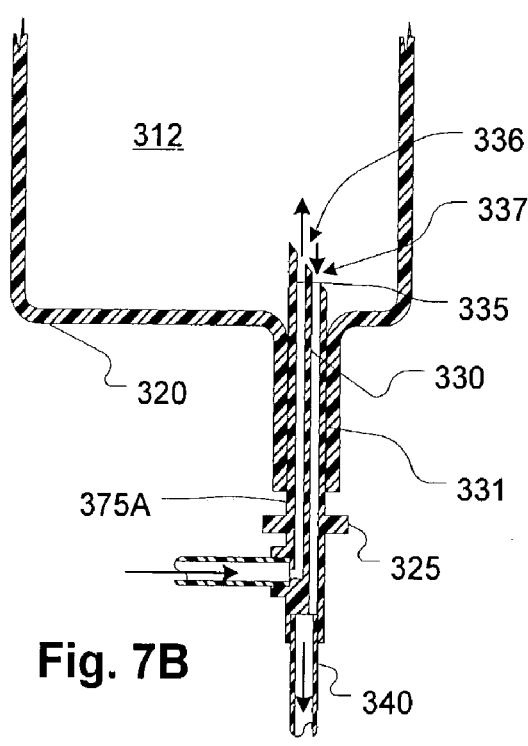
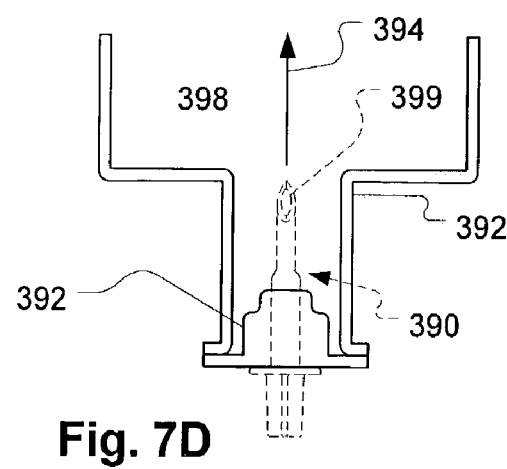
Fig. 7C
Fig. 7A
Fig. 7B
Fig. 7D

DUAL ACCESS SPIKE FOR INFUSATE BAGS

FIELD OF THE INVENTION

The invention generally relates to access used for providing two openings to a fluid container, for example, an infusible fluid bag such as saline.

BACKGROUND OF THE INVENTION

Air needs to be eliminated from many kinds of fluid circuits. For example, in extracorporeal blood circuits, air in replacement fluid that is injected into a patient can be hazardous. Typically; drip chambers are used in such circuits because these may serve as air traps. Another device is air-trapping filters. There exists a need for effective and convenient techniques for removing air from such circuits.

SUMMARY OF THE INVENTION

The invention provides systems and devices for handling air in a fluid processing circuit. U.S. patent application Ser. No. 09/905,171, incorporated by reference as if fully set forth herein in its entirety, describes systems for priming a replacement fluid circuit of a hemofiltration machine by recirculating fluid through a replacement fluid reservoir. Gas settles out of solution in the reservoir as the fluid is recirculated. The replacement fluid reservoir used in hemofiltration systems is commonly in the form of a fluid bag as used for sterile infusates such as saline or glucose solutions. To make a double-access to the bag to facilitate the recirculation, of the replacement fluid, a connector device is employed which consists, in part, of a bag spike with two flow channels. The single spike can be forced into a port that is sealed by a membrane until being perforated by the spike. Fluid flow out an inlet opening at the tip of the spike and is drawn from the bag through an outlet opening at the base of the spike.

One problem that may arise in connection with the spike discussed in the above application is that some fluid bags have long tube-shaped ports which surround the entire length of the spike so that the inlet and outlet openings both lie in a narrow tubular channel. The confinement of the outlet to the narrow channel can cause short-circuit flow that does not permit bubbles to settle out of the flow injected into the reservoir.

The present invention solves the problem of short-circuit flow in a double-access connector by various means, for instances, by providing that a distance between the outlet opening be located at a point within the greater interior volume of the bag. This can be achieved by extending the tip of the spike until it is long enough to reach outside the tube-shaped port of the fluid bag.

Various features of the double access spike provide for reliable insertion and use for recirculation. For example, the tip may be beveled to provide a sharp point that eases the piercing of the membrane. The outlet opening may be formed in a rounded or beveled surface located at the very tip. In addition, the inlet opening may be provided on a second beveled surface whose edges are rounded to allow it to pass through the membrane easily. In a preferred configuration, the beveled surface is conical to ease insertion. Another feature is that the lower portion is made substantially larger than the upper portion, the latter being so narrow as to not make a tight fit into the port. This requires that the spike be inserted all the way into the port to obtain a seal. The transition to a wide diameter base of the spike may be made an abrupt one and the inlet opening located sufficiently far away from the base to guarantee its placement in the larger volume of the bag. Other features and variations on the invention will be apparent from the detailed description below.

According to an embodiment, the invention is a multiple access container connector for use with fluid containers having elongated access extensions that has a body with an elongated shaft. The elongated shaft has a base, a tip, and an inlet orifice at the tip and an outlet orifice. The body has an inlet flow channel to couple for flow an inlet port at the base to the inlet orifice and an outlet flow channel to couple for flow an outlet port at the base to the outlet orifice. The elongated shaft has a length to ensure the inlet orifice is insertable beyond the elongated access extension.

In this embodiment, the body may have a base shaft substantially coaxial with the elongated shaft and located at the base, the base shaft having a diameter large enough to provide a compression seal with an opening of the elongated access neck. A transition portion of the body between the elongated shaft and the base shaft may be characterized by a progressively increasing cross-sectional area that is effective to ease a forcing of the connector through any obstacles in the elongated extension. The elongated shaft may have a diameter that is too small to provide a compression seal with an opening of the elongated access neck. The outlet opening may be located at the base. Where the body has a base shaft substantially coaxial with the elongated shaft and located at the base, the base shaft may have a diameter large enough to provide a compression seal with an opening of the elongated access neck. In such as, the elongated shaft may have a diameter that is too small to provide a compression seal with an opening of the elongated access neck. This ensures the connector is inserted well into the elongated access extensions of some fluid containers, such as fluid bags used for infusible fluids.

According to another embodiment, the invention is a connector for use with fluid containers having access ports with elongated necks. The connector has a body constructed for coupling to a fluid container, a first fluid passage in the body, a second fluid passage in the body that does not communicate with the first fluid passage. A first assembly communicating with the first fluid passage and including a first fitting to releasably couple the first fluid passage to an outlet of a fluid circuit and to convey fluid only through the first fluid passage is also provided. A second assembly communicates only with the second fluid passage and includes a second fitting to releasably couple the second fluid passage to an inlet of the fluid circuit. As a result, fluid can be circulated through the fluid container in a loop that includes the fluid circuit to collect in the fluid source air residing in the fluid circuit. The body has an elongated portion sufficiently long to ensure an outlet of the first fluid passage can reach into the fluid container and beyond a neck of the container.

In this embodiment, one end of the connector body may be tapered to form a spike. At least one of the first and second assemblies may include a luer fitting. At least one of the first and second assemblies may include an in-line clamp. The body may include a distal end communicating with the fluid source, wherein the first and second fluid passages each exits the distal end, and wherein the first fluid passage exits the distal end of the body at a higher gravity height that the second fluid passage exits the distal end. The base of the body near the releasable connectors may be wider than near the tip such that if the connector is not fully inserted in a port, the fluid will leak. This configuration may help to ensure the connector is fully inserted so the outlet is well within the container.

The invention may be embodied in several forms without departing from its spirit or essential characteristics. The scope of the invention is defined in the appended claims, rather than

BRIEF DESCRIPTION OF THE DRAWINGS

FIG. 2A is a plan view of a preferred embodiment of a double access spike.

FIG. 2B is a first side view of the spike of FIG. 2A.

FIG. 2C is a front view of the spike of FIGS. 2A and 2B.

FIG. 2D is bottom view of the spike of FIG. 2A-C.

FIG. 2E is a second side view of the spike of FIG. 2A-D.

FIG. 2F is a section view of the spike of FIGS. 2A-E taken along the section shown in FIG. 2E.

FIG. 3A is a bottom oblique view of the spike of FIGS. 2A-F.

FIG. 3B is a top oblique view of the spike of FIGS. 2A-F and 3A.

FIG. 3C is a side view of a spike with a conical transition from an elongated shaft portion to a base shaft portion.

FIGS. 7A and 7B are illustrations of an elongated access spike with inlet and outlet openings that are both near a tip thereof.

FIG. 7C illustrates a variation of the embodiment of FIGS. 7A and 7B with a wide base portion on a shaft thereof.

FIG. 7D illustrates a spike with an elongated shaft that is not quite long enough to reach within a container, but which is near a boundary such that flow is not retarded by the port tube.

DESCRIPTION OF THE PREFERRED EMBODIMENT

Figure 1A:
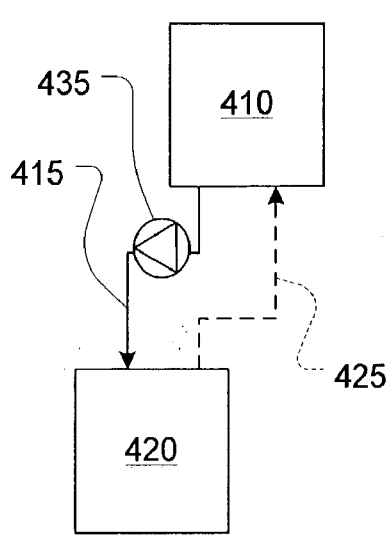
FIG. 1A illustrates a fluid circuit and fluid reservoir or tank coupled to circulate fluid and thereby eliminate gases in fluid or other light constituents.

Referring to FIG. 1A, a fluid reservoir 410 supplies fluid via a supply channel 415 to a fluid circuit represented schematically at 420. The fluid circuit 420 may be a blood treatment systems such as dialysis or hemofiltration. Fluid may be conveyed with the assistance of a pump 435, which, although shown separately may form part of the fluid circuit 420. The fluid reservoir 410 may be connected temporarily to allow a return flow 425 and may employ two accesses to the reservoir 410.

Figure 1B:
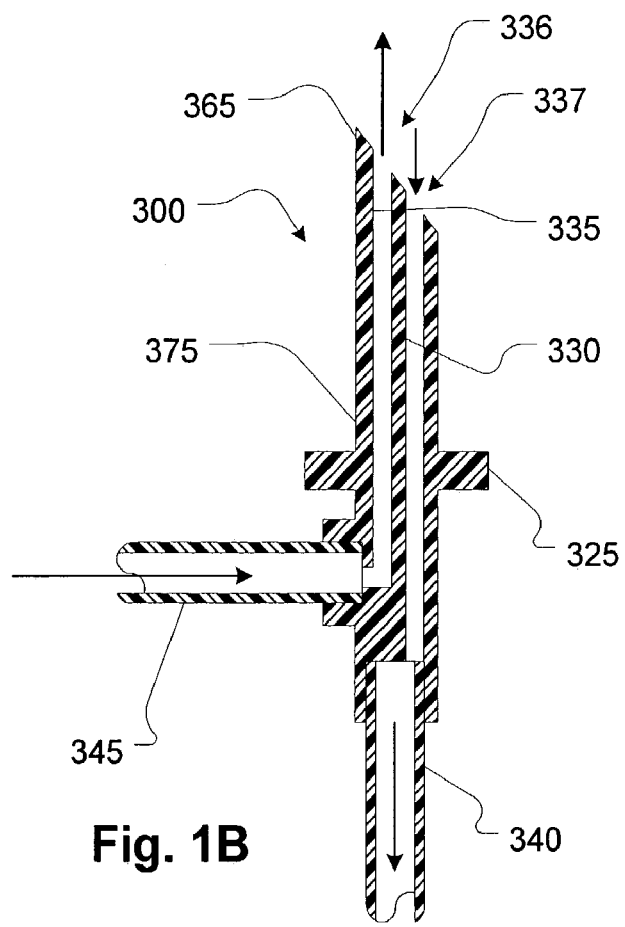
FIG. 1B is an illustration of a double access spike with ports that may be susceptible to short circuit flow when used in a narrow channel.

Referring now to FIG. 1B, a spike shown generally at 300, has a pointed tip 365 and inlet and outlet openings 336 and 337, respectively, near the tip 365. A handle portion 325 facilitates insertion of the spike 300 into a container port (not shown in this figure, but described below). An inlet tube 345 supplies fluid through a channel 335 to the inlet opening 336. An outlet tube 340 draws fluid through a channel 330 from the outlet opening 337. An elongated shaft 375 has a uniform diameter for sealing in the container port.

Figure 1C:
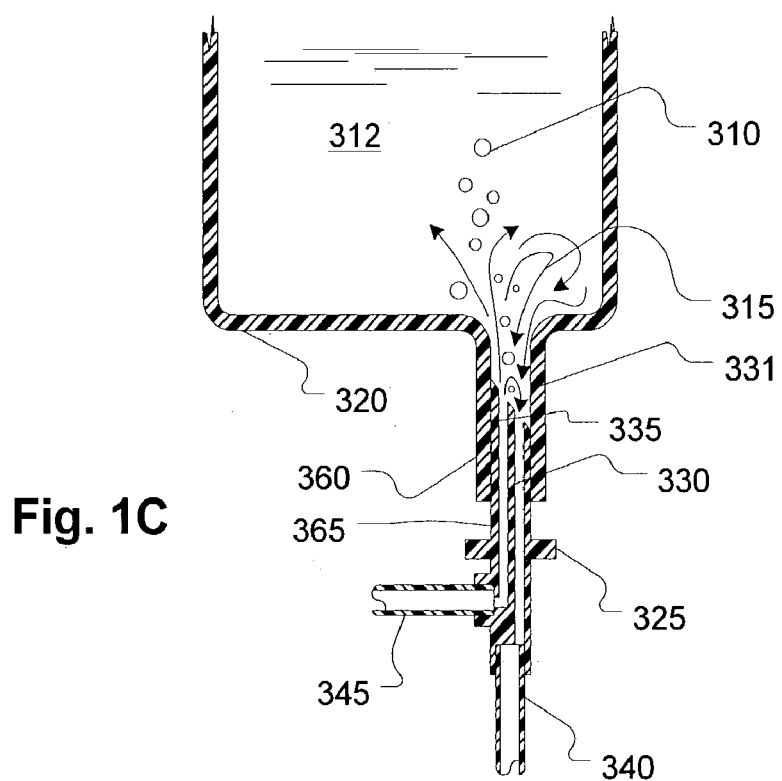
FIG. 1C is an illustration of a double access spike in a fluid bag port with a narrow channel.

Referring now also to FIG. 1C, a container 320 has a port tube 360 into which the shaft 375 is forced to form a seal and provide communication between the inlet tube 345 and the outlet tube 340 and the interior of the container 320. The tube port 360 of the container 320 is common in fluid bags used for infusible fluids such as saline solution and other medical fluids. Fluid flows into a greater interior 312 of the container 320 where bubbles 310 may settle out into the container 320 thereby reducing the amount of bubbles in the fluid leaving through the outlet opening 337. For some fluid circuits, such a removal process may be performed prior to a treatment, as described in the patent application incorporated by reference above.

Some manufacturers of containers 320, such as fluid bag-types, provide port tubes 360 that are much longer than others. As a result, for some types, the tip 365 may not extend into the greater interior 312. When that occurs, fluid entering the container 320 from the inlet opening 336 may take a short-circuit path into the outlet opening 337. This is due, in part, to the fact that the outlet flow from the outlet opening 336 is confined within an interior flow space 331 defined by the port tube 360. The high flow resistance overcomes the inertia of the initial flow slowing it down and keeping the outlet flow close to the suction zone of the flow back into inlet opening 337.

Referring to FIGS. 2A-3D and 3A and 3B, a double-access spike 10 has an elongated extension shaft portion 22 that is substantially circular in cross-section with a single outlet port 18 at a tip 24 thereof. An inlet port 20 is located adjacent a base shaft portion 14 that has a substantially larger diameter than the extension shaft portion 22. Each of the inlet and outlet ports 18 and 20 communicates with inlet and outlet connection ports 34 and 36, respectively.

A shelf 12 facilitates a user's ability to grasp the spike 10 and force it into a port (shown in FIGS. 4A and 4B and discussed below). Flange portions 32 provide structural rigidity. Tubing (not shown) may be inserted into the ports 34 and 36 and bonded to the ports 34 and 36 and later plugged and sterilized as a unit. A sloped and curved portion 28 allows the base shaft portion 14 to be forced easily through any cover, such as a membrane (not shown) or other covering that might be present in the container port. An alternative embodiment of the sloped and curved portion 28 is shown in FIG. 3C. In that embodiment, a conical portion 28A provides a similar function and may be advantageous in terms of ease of use.

A protrusion 33 may be incorporated on the outside of the extension shaft portion 22 to cut through any sealing material that might seal around the extension shaft portion 22 thereby allowing a user to force the spike 10 less than fully into a container port (not shown). This is explained in connection with FIGS. 4A and 4B, below.

The spike 22 may be supplied as part of a complete fluid circuit as described in the patent application incorporated by reference above. The spike 10 may be manufactured from injection-molded plastic material. It may be formed in one or more parts of identical or different materials. For medical applications, the spike 10 is preferably made from bio-compatible materials.

Figure 4A:
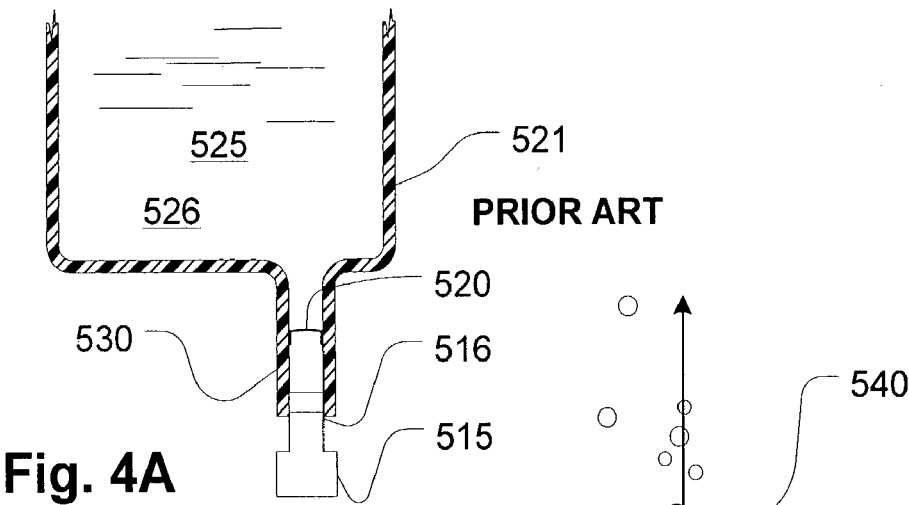
FIG. 4A illustrates a fluid container with a port protected by a removable plug and a puncturable membrane.

Referring to FIG. 4A, a typical fluid container in the form of a fluid bag 521 has a port extension 530 with an access 516 protected by a removable plug 515. A membrane 520 maintains the container 521 in a sealed state, protecting contents 525, until the membrane 520 is punctured by a conventional spike or one such as spike 10 of the foregoing figures.

Figure 4B:
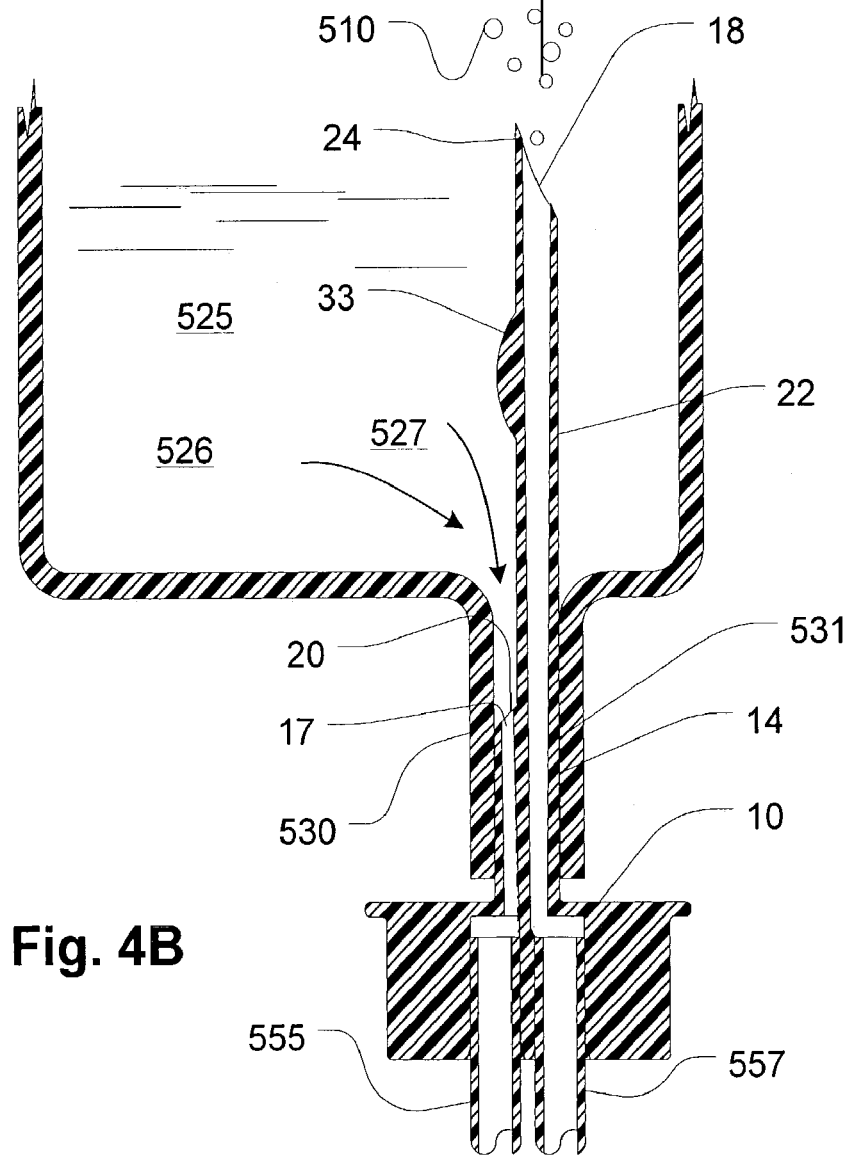
FIG. 4B illustrates the fluid container of FIG. 4A with the spike of FIGS. 2A-F and 3A-B inserted in the port.

Referring now also to FIG. 4B, the sealed container 521 membrane 520 is shown after accessing using a spike 10 as illustrated in the foregoing figures. The extension shaft portion 22 extends well into an interior 526 of the container 521. The protrusion 33 ensures that the membrane 520 is sufficiently disrupted—stretched or cut—upon insertion of the extension shaft portion 22 through the port extension 530 that fluid 525 will leak unless the base shaft portion 14 is forced well into the access 516. If the base shaft portion 14 is sized to form a seal with the access 516, then the penetration of the extended shaft portion 22 will be ensured, assuming that the user is motivated to avoid leaks.

By ensuring the extended shaft portion 22 extends well into the interior volume 526, the inlet opening 18 may be certain to be located well within the interior 526 and well beyond an interior 531 of the port shaft 530. This helps to ensure against short-circuit flow because the momentum of an inlet flow 540 carries any gases well inside the interior volume 526 thereby substantially avoiding a suction zone 527 near the outlet opening 20 created by an outlet flow through the outlet opening 20.

Figure 5:
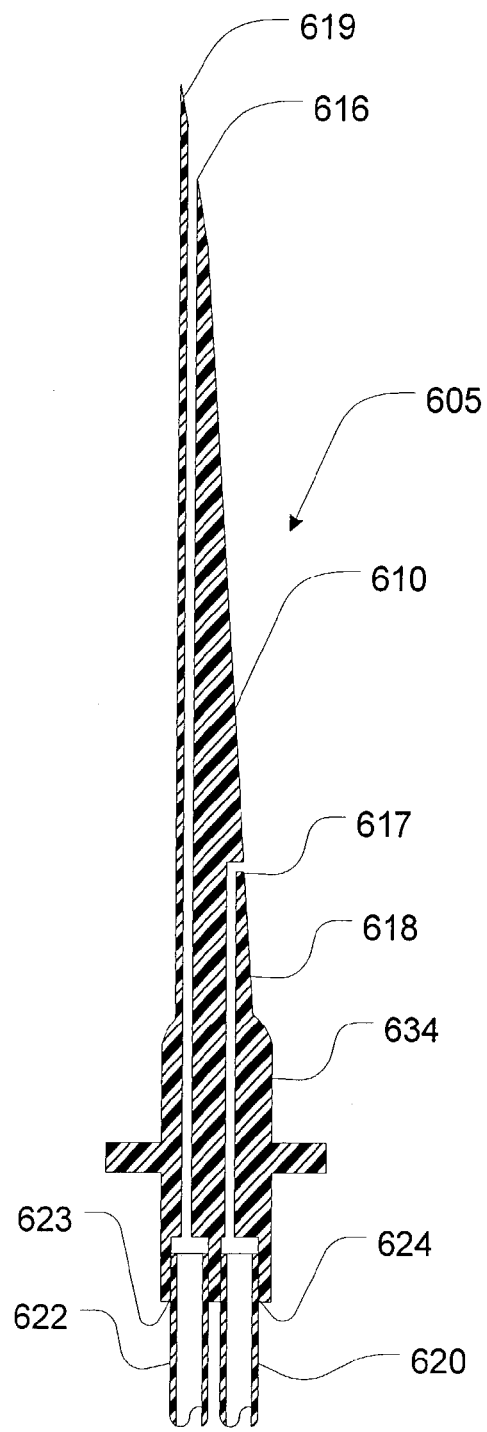
FIGS. 5 and 6 illustrate two further embodiments of dual access spikes.

Referring now to FIG. 5, another embodiment of a double access spike 605 has a tapered shaft 610 with an inlet opening 616 near its tip 619 and an outlet opening 617 near its base 618. Inlet and outlet ports 623 and 624 are provided for attachment of respective tubes 622 and 620. A base portion 634 is provided to ensure that the spike 605 is inserted well into a port (e.g. 516 of FIG. 4A).

Figure 6:
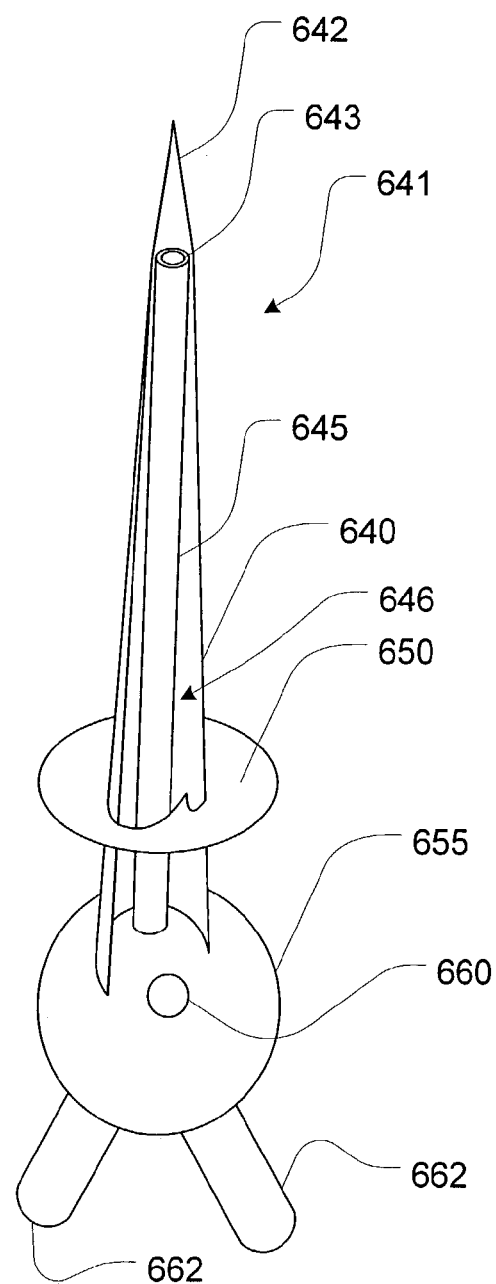

Referring to FIG. 6, yet another embodiment of a double access spike 641 has a cone-shaped forming a tapered shaft 640 that is open to hold a tube 645 therewithin. An inlet opening 643 at the end of the tube 645 is near the tip 642 of the shaft 640. An outlet opening 660 is provided in a spherical base portion 655. The inlet and outlet openings 643 and 660 communicate with respective ports 662 and 662. The diameter of the base portion 655 ensures that the spike 641 is inserted well into a port (e.g. 516 of FIG. 4A). The open shape of the shaft 640 forms a recess 646 within whose blind end the tube 645 resides and whose access ensures that fluid 525 (FIG. 4A) in the container interior 526 (FIG. 4A) is able to reach the opening 660. This is so because the shaft 640 creates an opening in the membrane 650 if present.

Referring again to 1B and 1C and also to FIGS. 7A and 7B, depending upon the size and shape of the container 320, it may be possible in many cases to avoid short-circuit flow solely by means of placing the outlet opening 336 well into the greater volume 312 of the container. This may be achieved by extending the shaft 375 of the spike 300 so until it is long enough to ensure the outlet opening 336 is well outside the interior flow space 331 of the port tube 330. An embodiment 300A with such an extended shaft 375A is shown in FIGS. 7A and 7B. The other features of the embodiment of FIGS. 7A and 7B are the same as those of FIGS. 1B and 1C. The extension of the outlet opening 336 into the larger interior space 312 allows the outlet flow's momentum to carry it far away from the return flow out through the outlet opening 337.

A refinement of the embodiment of FIGS. 7A and 7B is illustrated in FIG. 7C. A spike 700 has an elongated shaft 770 that is long enough to bring inlet and outlet openings 777 and 778 well beyond the narrow flow space of some fluid bags. But the shaft 770, unlike the embodiments of FIGS. 1B, 1C, 7A, and 7B, has a shaft 770 that is too narrow to seal the port tube (not shown in FIG. 7C, but as described with reference to other figures). A wider base shaft portion 780 seals the port tube. This ensures a user will force the spike 700 well into the port tube thereby ensuring the outlet opening is beyond the narrow flow space defined by the flow tube.

Referring to FIG. 7D, the reach of a spike 390 may not have to be all the way into a fluid container 396 to avoid short-circuit flow. If the length is such as to reduce flow friction within a port tube 392 of the container 396, then the inlet flow will not be subject to crossflow. How close an outlet 399 has to be to a greater interior 398 of the container 396 may depend on the diameter of the port tube 392 and other considerations, the crucial issue being whether there is sufficient momentum relative to frictional losses (both turbulent and viscous) to provide that most of the gases in the inlet flow will avoid being sucked back into the outlet flow. However, although it may be overkill in some cases, this can be assured by placing the outlet 399 well away from the port tube 392, although shorter lengths such as illustrated in FIG. 7D are considered to be within the scope of the invention.

Referring back to Figs. FIGS. 2A-3D and 3A and 3B, in a preferred embodiment of the invention, the distance from the shelf 12 to the inlet opening 24 is about 2 to 2.5 inches while that from the shelf 12 to the outlet opening 20 is about half an inch. In a broader definition of a preferred embodiment, the lengths are chosen such as to be compatible with fluid containers currently having an inlet tube of 1.5 inch length or more.

While not specifically described above, variations on the above embodiments can benefit from various of the features described above. For example, an outlet opening a tip of a spike need not face in an upward direction, but may also be configured to eject flow sideways into a fluid container. Also, the number of accesses is not necessarily limited to two. The configuration features described can be applied in spikes with more than two openings connected to various different fluid circuits or joined to common fluid circuits. Also, the seal between the spike and bag need not be a compression seal as illustrated in the above embodiments. For example, a luer-type connector could be used or any other type of fitting. Also, while a sharp spike is described above, in some applications, a sharp point may be superfluous. For example, where a container does not require the puncturing, for example of a membrane, a sharp tip may not be useful.

It will be evident to those skilled in the art that the invention is not limited to the details of the foregoing illustrative embodiments, and that the present invention may be embodied in other specific forms without departing from the spirit or essential attributes thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A device for providing a recirculating flow, comprising:
a shaft having a shaft axis, a base end and a tip;
an inlet orifice proximate the tip;
the shaft having an elongate section terminating at the tip with a wider portion closer to the base end;
the wider portion being shaped such that it has a constant cross-sectional shape over a substantial portion of the length of the wider portion;
a transition between the elongate section and the wider portion, the transition having an outlet orifice spaced from the wider portion; and
inlet and outlet lumens extending along the shaft,
wherein the elongate section has a cutting edge extending in an axial direction above a surface of the elongate section.

2. A device as in claim 1, further comprising an inlet port and an outlet port, wherein the inlet lumens connects the inlet port to the inlet orifice, the outlet lumens connects the outlet port to the outlet orifice, and the inlet and outlet ports have respective cylindrical recesses for receiving tubing.

3. A device as in claim 1, further comprising inlet and outlet ports at the base end connected to the inlet and outlet lumens, respectively, and attached to flexible tubing.

4. A device as in claim 1, wherein the outlet orifice faces the tip.

5. A device as in claim 1, wherein the outlet orifice is formed in a step between the wider portion and the elongate section.

6. A device as in claim 5, wherein the step has a surface having a normal that is angled with respect to the shaft axis.

7. A device as in claim 5, comprising inlet and outlet ports having cylindrical recesses for receiving tubing, wherein the base end has a flat flange extending outwardly in a radial direction from the wider portion, the inlet and outlet port cylindrical recesses have respective accesses, and the flat flange is located remote, in the axial direction, from the accesses.

8. A device for providing a recirculating flow, comprising:
a shaft having a shaft axis, a base end and a tip;
an inlet orifice proximate the tip;
the shaft having an elongate section terminating at the tip with a wider portion closer to the base end;
the wider portion being shaped such that, at least at a point remote from the base end, the wider portion has a constant circular cross-section over a substantial portion of the length of the wider portion;
a transition between the elongate section and the wider portion, the transition having an outlet orifice spaced from the wider portion; and
inlet and outlet lumens extending along the shaft,
wherein the elongate section has a cutting edge extending in an axial direction above or below a surface of the elongate section.

9. A device as in claim 8, further comprising an inlet port and an outlet port, wherein the inlet lumens connects the inlet port to the inlet orifice, the outlet port connects the outlet port to the outlet orifice, and the inlet and outlet ports have respective cylindrical recesses for receiving tubing.

10. A device as in claim 8, further comprising inlet and outlet ports at the base end connected to the inlet and outlet lumens, respectively, and attached to flexible tubing.

11. A device as in claim 8, wherein the outlet orifice faces the tip.

12. A device as in claim 8, wherein the outlet orifice is formed in a step between the wider portion and the elongate section.

13. A device as in claim 12, wherein the step has a surface having a normal that is angled with respect to the shaft axis.

14. A device as in claim 12, comprising inlet and outlet ports having cylindrical recesses for receiving tubing, wherein the base end has a flat flange extending outwardly in a radial direction from the wider portion, the inlet and outlet port cylindrical recesses have respective accesses, and the flat flange is located remote, in the axial direction, from the accesses.

15. A device for providing a recirculating flow, comprising:
a shaft having:
an elongate portion extending from a base end of the shaft to a tip of the shaft;
a wider portion extending from the base end to a location between the base end and the tip;
a transition section between the elongate portion and the wider portion;
a first orifice located proximal to the tip of the shaft;
a second orifice located on a surface of the transition section; and
first and second lumens extending along the shaft so as to respectively connect the first and second orifices with corresponding first and second ports at the base end;
wherein the elongate portion has a membrane disruption portion between the tip and the transition, wherein the membrane disruption portion is arranged to cut the membrane upon insertion of the elongate portion of the shaft through said membrane.

16. A device as in claim 15, wherein the membrane disruption portion includes an axially-extending protrusion on an exterior of the elongate portion of the shaft.

17. A device as in claim 15, wherein the membrane disruption portion is arranged on the elongate portion of the shaft so as to disrupt a sealing function of a membrane of a sealed container upon insertion of the membrane disruption portion through said membrane.

18. A device as in claim 17, wherein the wider portion is constructed to seal the disrupted membrane when the shaft is fully inserted into the sealed container.

19. A device as in claim 18, wherein the wider portion is arranged such that the disrupted membrane is not sealed when the shaft is only partially inserted into the sealed container.

* * * * *